United States Patent
Dall'Occo et al.

(10) Patent No.: US 6,822,106 B2
(45) Date of Patent: Nov. 23, 2004

(54) PREPARATION OF ETHYLENE POLYMERS

(75) Inventors: Tiziano Dall'Occo, Ferrara (IT); Ofelia Fusco, Ferrara (IT); Maurizio Galimberti, Milan (IT); Ilya Nifant'ev, Moscow (RU); Ilya Laishevtsev, Moscow (RU)

(73) Assignee: Basell Poliolefine Italia S.p.A., Milan (IT)

( * ) Notice: Subject to any disclaimer, the term of this patent is extended or adjusted under 35 U.S.C. 154(b) by 0 days.

(21) Appl. No.: 10/700,095

(22) Filed: Nov. 3, 2003

(65) Prior Publication Data

US 2004/0097669 A1 May 20, 2004

Related U.S. Application Data

(62) Division of application No. 09/914,411, filed as application No. PCT/EP00/13346 on Dec. 21, 2000.

(30) Foreign Application Priority Data

Dec. 28, 1999 (EP) .............................................. 99204565

(51) Int. Cl.$^7$ ................................................. C08F 4/64
(52) U.S. Cl. .................... 556/53; 526/161; 526/943; 502/155; 556/53; 549/29; 549/59; 549/60
(58) Field of Search .................. 526/161; 502/155; 556/53; 549/29, 59, 60

(56) References Cited

FOREIGN PATENT DOCUMENTS

| | | | |
|---|---|---|---|
| EP | 0632066 | 1/1995 | ......... C08F/210/16 |
| EP | 0633272 | 1/1995 | .......... C08F/10/02 |
| EP | 0720629 | 7/1996 | ......... C08F/295/00 |
| EP | 0742801 | 11/1996 | ......... C08F/297/08 |
| WO | 9200333 | 1/1992 | ............. C08F/4/76 |
| WO | 9526369 | 10/1995 | .......... C08F/10/00 |
| WO | 9532995 | 12/1995 | .......... C08F/10/00 |
| WO | 9822486 | 5/1998 | .......... C07F/17/00 |
| WO | 9921899 | 5/1999 | .......... C08F/10/02 |
| WO | 0121674 | 3/2001 | .......... C08F/10/00 |

OTHER PUBLICATIONS

C. J. Carman et al., "Monomer Sequence Distribution in Ethylene–Propylene Rubber Measured by $^{13}$C NMR 3. Use of Reaction Probability Model[1]," *Macromolecules*, 10(3): 536–544 (1977).

M. Kakugo et al., "$^{13}$C NMR Determination of Monomer Sequence Distribution in Ethylene–Propylene Copolymers Prepared with δ–TiCl$_3$–Al(C$_2$H$_5$)$_2$Cl;" *Macromolecules*, 15: 1150–1152 (1982).

J. A. Ewen, "Polymerization Catalysts with Cyclopendadienyl Ligands Ring–Fused to Pyrrole and Thiophene Heterocycles," *J. Am. Chem. Soc.*, 120: 10786–10787 (1998).

E. Hey–Hawkins, "Bis(cyclopentadienyl)zirconium(IV) or –hafnium(IV) Compounds with Si–, Ge–, Sn–, N–, P–, As–, Sb–, O–, S–, Se–, Te–, or Transition Metal–Centered Anionic Ligands," *Chem. Rev.*, 94: 1661–1717 (1994).

Application Ser. No. 09/914,304 filed Aug. 27., 2001; "Heterocyclic Metallocene Compounds and Use Thereof in Catalyst Systems for Product Olefine Polymers"—US 18023/5420.

*Primary Examiner*—Caixia Lu

(57) ABSTRACT

Ethylene based polymers having high molecular weights can be obtained in high yields at temperatures of industrial interest, by carrying out the polymerization reaction in the presence of catalysts comprising silicon bridged metallocenes having a particular ligand system containing a heteroatom.

5 Claims, No Drawings

PREPARATION OF ETHYLENE POLYMERS

CROSS-REFERENCE TO RELATED APPLICATIONS

This application is a divisional of co-pending application Ser. No. 09/914,411, filed on Aug. 28, 2001, which is a national phase filing under 35 U.S.C. §371 of International Application No. PCT/EP00/13346 filed Dec. 21, 2000, which claims priority to EP Application No. 99204565.8 filed Dec. 28, 1999. The entire contents of application Ser. No. 09/914,411, International Application No. PCT/EP00/13346 and EP Application No. 99204565.8, each as filed, are incorporated herein by reference.

The present invention relates to a polymerization process for the preparation of ethylene polymers in the presence of a metallocene catalyst. The invention also relates to a process for the preparation of the relevant metallocenes and of the corresponding ligands, which are useful as intermediates in the synthesis of said metallocene compounds. The invention further relates to ethylene copolymers obtainable with those metallocene catalysts.

Metallocene compounds having two bridged cyclopentadienyl or indenyl groups are known as catalyst components for the homo- and copolymerization reaction of ethylene.

Also known are metallocene compounds containing a bridged bis-fluorenyl ligand system for use in the polymerization of olefins.

For instance, in EP-A-0 632 066 it is discloses the use of bis-fluorenyl based metallocenes for the production of elastomeric copolymers of ethylene with propylene.

More recently, heterocyclic metallocene compounds used in the polymerization of alpha-olefins have been disclosed.

For example, PCT application WO 98/22486 discloses metallocenes containing a cyclopentadienyl radical directly coordinating the central metal atom, to which are fused one or more rings containing at least one heteroatom. These metallocenes, in combination with a suitable cocatalyst, are used in the polymerization of olefins such as ethylene. However, the molecular weight that can be obtained is still not sufficient for many uses and the activity of the catalyst systems containing said metallocenes, when used in the polymerization of ethylene, is not satisfactory.

It would be desirable to identify metallocene catalysts capable of yielding ethylene polymers having a high molecular weight and which also have high activities, such that the amount of the catalyst remaining in the polymer is minimized. Further, it would be advantageous to obtain copolymers of ethylene with alpha-olefins and polyenes in which the comonomer units in the polymeric chain are homogeneously distributed.

It has been found unexpectedly that it is possible to achieve the above and other results by carrying out the polymerization reaction of ethylene in the presence of a catalyst based on a class of heteroatom containing metallocene compounds.

Thus, according to a first aspect of the present invention a process is provided for the preparation ethylene polymers, comprising the polymerization reaction of ethylene and optionally one or more olefins in the presence of a catalyst comprising the product obtainable by contacting:

(A) a metallocene compound of the general formula (I):

$$SiR^1R^2LQMX_p \qquad (I)$$

wherein $SiR^1R^2$ is a divalent group bridging the moieties L and Q;

$R^1$ and $R^2$, which may be the same or different, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radical optionally containing heteroatoms belonging to groups 13 or 15–17 of the Periodic Table of the Elements; optionally $R^1$ and $R^2$ form a ring comprising from 3 to 8 atoms, which can bear substituents;

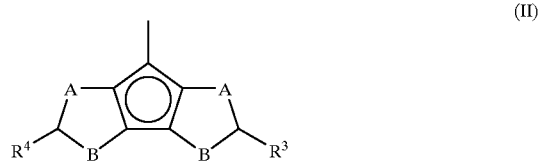

(II)

wherein A and B are selected from sulfur (S), oxygen (O) and $CR^5$, $R^5$ is selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals optionally containing heteroatoms belonging to groups 13 or 15–17 of the Periodic Table of the Elements; and wherein the rings containing A and B have a double bond in the allowed position having an aromatic character, either A or B being different from $CR^5$ i.e. if A is S or O, B is $CR^5$ or if B is S or O, A is $CR^5$;

$R^3$ and $R^4$, which may be the same or different, are selected from hydrogen a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radical optionally containing heteroatoms belonging to groups 13 or 15–17 of the Periodic Table of the Elements; preferably $R^3$ and $R^4$, which may be the same or different, are selected from a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radical optionally containing heteroatoms belonging to groups 13 or 15–17 of the Periodic Table of the Elements;

L is a moiety of formula (III):

(III)

wherein $R^6$, $R^7$, $R^8$ and $R^9$, which may be the same or different, are selected from $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals optionally containing heteroatoms belonging to groups 13 or 15–17 of the Periodic Table of the Elements; and two adjacent $R^6$ and $R^7$ and/or $R^8$ and $R^9$ can form a ring comprising from 3 to 8 atoms, which can include heteroatoms belonging to groups 13 or 15–17 of the Periodic Table of the Elements and can bear substituents;

M is an atom of a transition metal selected from those belonging to group 3, 4, 5, 6 or to the lanthanide or actinide groups in the Periodic Table of the Elements (new IUPAC version), X, which may be the same or different, is a ligand selected from hydrogen, halogen, $R^{10}$, $OR^{10}$, $OSO_2CF_3$, $OCOR^{10}$, $SR^{10}$, $NR^{10}_2$ or $PR^{10}_2$ group, wherein $R^{10}$ is selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radical, optionally containing heteroatoms belonging to groups 13 or 15–17 of the Periodic Table of the Elements;

p is an integer of from 0 to 3, preferably from 1 to 3 being equal to the oxidation state of the metal M minus 2 and (B) an alumoxane and/or a compound capable of forming an alkyl metallocene cation.

The transition metal M is preferably selected from titanium, zirconium and hafnium preferably in the formal oxidation state of +4. Most preferably zirconium is used. Preferably p is 2.

The X substituents are preferably chloride or methyl groups.

Preferably the substituents $R^1$ and $R^2$ are $C_1$–$C_{20}$-alkyl groups such as methyl group; $R^3$ and $R^4$ are $C_1$–$C_{20}$-alkyl groups optionally containing silicon atoms or $C_6$–$C_{20}$-aryl groups, such as methyl, tert-butyl, phenyl, trimethylsilyl groups; $R^6$, $R^7$, $R^8$ and $R^9$ are $C_1$–$C_{20}$-alkyl groups such as methyl, tertbutyl, A is sulfur and B is CH.

A further object of the present invention is a metallocene compound of formula (I)

$$SiR^1R^2LQMX_p \qquad (I)$$

Wherein $R^1$, $R^2$, L, Q, M, X and p are described above.

Non-limiting examples of metallocene compounds suitable for use in the process of the invention are:

dimethylsilandiyl-(tetramethylcyclopentadienyl)-7-(2,5-dimethylcyclopentadienyl-[1,2-b:4,3-b']-dithiophene) zirconium dichloride and dimethyl, dimethylsilandiyl-(tetraethylcyclopentadienyl)-7-(2,5-dimethylcyclopentadienyl-[1,2-b:4,3-b']-dithiophene) zirconium dichloride and dimethyl, dimethylsilandiyl-(tetraethylcyclopentadienyl-7-(2,5-dimethylcyclopentadienyl-[1,2-b:4,3-b']-dithiophene) zirconium dichloride and dimethyl, dimethylsilandiyl-7-(2,5-dimethyl-cyclopentadienyl-[1,2-b:4,3-b']-dithiophene)-7-(cyclopentadienyl-[1,2-b:4,3-b']-dithiophene)zirconium dichloride and dimethyl, dimethylsilandiyl-7-(2,5-diethyl-cyclopentadienyl-[1,2-b:4,3-b']-dithiophene)-7-(cyclopentadienyl-[1,2-b:4,3-b']-dithiophene)zirconium dichloride and dimethyl, dimethylsilandiyl-7-(2,5-diisopropyl-cyclopentadienyl-[1,2-b:4,3-b']-dithiophene)-7-(cyclopentadienyl-[1,2-b:4,3-b']-dithiophene)zirconium dichloride and dimethyl, dimethylsilandiyl-7-(2,5-ditertbutyl-cyclopentadienyl-[1,2-b:4,3-b']-dithiophene)-7-(cyclopentadienyl-[1,2-b:4,3-b']-dithiophene)zirconium dichloride and dimethyl, dimethylsilandiyl-7-(2,5-ditrimethylsilyl-cyclopentadienyl-[1,2-b:4,3-b']-dithiophene)-7-(cyclopentadienyl-[1,2-b:4,3-b']-dithiophene) zirconium dichloride and dimethyl, dimethylsilandiyl-7-(2,5-dimethyl-cyclopentadienyl-[1,2-b:4,3-b']-dithiophene)-7-(tetramethylcyclopentadienyl-[1,2-b:4,3-b']-dithiophene)zirconium dichloride and dimethyl, dimethylsilandiyl-7-(2,5-diethyl-cyclopentadienyl-[1,2-b:4,3-b']-dithiophene)-7-(tetramethylcyclopentadienyl-[1,2-b:4,3-b']-dithiophene)zirconium dichloride and dimethyl, dimethylsilandiyl-7-(2,5-diisopropyl-cyclopentadienyl-[1,2-b:4,3-b']-dithiophene)-7-(tetramethylcyclopentadienyl-[1,2-b:4,3-b']-dithiophene)zirconium dichloride and dimethyl, dimethylsilandiyl-7-(2,5-diisopropyl-cyclopentadienyl-[1,2-b:4,3-b']-dithiophene)-7-(tetramethylcyclopentadienyl-[1,2-b:4,3-b']-dithiophene)zirconium dichloride and dimethyl, dimethylsilandiyl-7-(2,5-dimethyl-cyclopentadienyl-[1,2-b:4,3-b']-dithiophene)-7-(3-trimethylsilylcyclopentadienyl-[1,2-b:4,3-b']-dithiophene)-zirconium dichloride and dimethyl, dimethylsilandiyl-7-(2,5-dimethyl-cyclopentadienyl-[1,2-b:4,3-b']-dithiophene)-9-(fluorenyl)-zirconium dichloride and dimethyl, b:3,4-b']-dithiophene) zirconium dichloride and dimethyl.

Particularly interesting metallocenes of formula (I) for use in the process of the invention are those in which L is a moiety of formula (IV):

(IV)

$R^{14}$ $R^{14}$
$R^{11}$ $R^{11}$
$R^{12}$ $R^{12}$
$R^{13}$ $R^{13}$ wherein $R^{14}$, $R^{11}$, $R^{12}$ and $R^{13}$, which may be the same or different, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radical optionally containing heteroatoms belonging to groups 13 or 15–17 of the Periodic Table of the Elements, and optionally two adjacent $R^{14}$, $R^{11}$, $R^{12}$ and $R^{13}$ groups can form a ring having 3 to 8 atoms, which can bear substituents. Preferably $R^{14}$, $R^{12}$ and $R^{13}$ are hydrogen and $R^{11}$ are selected from hydrogen and a $C_1$–$C_{20}$-alkyl group.

Most preferably $R^{11}$ is selected from hydrogen and a tert-butyl radical.

Non-limiting examples belonging to this class are:

dimethylsilandiyl-7-(2,5-dimethyl-cyclopentadienyl-[1,2-b:4,3-b']-dithiophene)-9-(fluorenyl)-zirconium dichloride and dimethyl, dimethylsilandiyl-7-(2,5-diethyl-cyclopentadienyl-[1,2-b:4,3-b']-dithiophene)-9-(fluorenyl)-zirconium dichloride and dimethyl, dimethylsilandiyl-7-(2,5-diisopropyl-cyclopentadienyl-[1,2-b:4,3-b']-dithiophene)-9-(fluorenyl)-zirconium dichloride and dimethyl, dimethylsilandiyl-7-(2,5-dimethyl-cyclopentadienyl-[1,2-b:4,3-b']-dithiophene)-9-(2,7-dimethylfluorenyl)-zirconium dichloride and dimethyl, dimethylsilandiyl-7-(2,5-dimethyl-cyclopentadienyl-[1,2-b:4,3-b']-dithiophene)-9-(2,7-diethylfluorenyl)-zirconium dichloride and dimethyl, dimethylsilandiyl-7-(2,5-dimethyl-cyclopentadienyl-[1,2-b:4,3-b']-dithiophene)-9-(2,7-diisopropylfluorenyl)-zirconium dichloride and dimethyl, dimethylsilandiyl-7-(2,5-dimethyl-cyclopentadienyl-[1,2-b:4,3-b']-dithiophene)-9-(2,7-ditertbutylfluorenyl)-zirconium dichloride and dimethyl.

Other interesting metallocenes of formula (I) for use in the process of the invention are those in which L is a moiety of formula (II'):

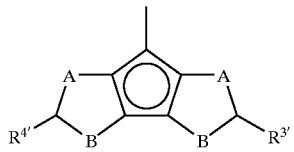

(II')

wherein A and B are defined as above, $R^{3'}$ and $R^{4'}$, which may be the same or different, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radical optionally containing heteroatoms belonging to groups 13 or 15–17 of the Periodic Table of the Elements;

Preferred compounds are those, in which A is sulfur and B is a CH group, $R^{3'}$ and $R^{4'}$ are selected from a $C_1$–$C_{20}$-alkyl group.

Most preferably $R^{3'}$ and $R^{4'}$ are methyl groups.

Non-limiting examples belonging to this class are:

dimethylsilandiylbis-7-(2,5-dimethyl-cyclopentadienyl-[1,2-b:4,3-b']-dithiophene)zirconium dichloride and dimethyl, dimethylsilandiylbis-7-(2,5-diethyl-cyclopentadienyl-[1,2-b:4,3-b']-dithiophene)zirconium dichloride and dimethyl, dimethylsilandiylbis-7-(2,5-diisopropyl-cyclopentadienyl-[1,2-b:4,3-b']-dithiophene)zirconium dichloride and dimethyl, dimethylsilandiylbis-7-(2,5-diterbutyl-cyclopentadienyl-[1,2-b:4,3-b']-dithiophene)zirconium dichloride and dimethyl.

The alumoxane used as component (B) can be obtained by reacting water with an organo-aluminium compound of formula $H_jAlR^{15}{}_{3-j}$ or $H_jAl_2R^{15}{}_{6-j}$, where the $R^{15}$ substituents, which may be the same or different, are hydrogen atoms, $C_1$–$C_{20}$-alkyl, $C_3$–$C_{20}$-cyclalkyl, $C_6$–$C_{20}$-aryl, $C_7$–$C_{20}$-alkylaryl or $C_7$–$C_{20}$-arylalkyl, optionally containing silicon or germanium atoms with the proviso that at least one $R^{15}$ is different from halogen, and J ranges from 0 to 1, being also a non-integer number. In this reaction the molar ratio of Al/water is preferably comprised between 1:1 and 100:1.

The molar ratio between aluminium and the metal of the metallocene is comprised between about 10:1 and about 20000:1, and more preferably between about 100:1 and about 5000:1.

The alumoxanes used in the catalyst according to the invention are considered to be linear, branched or cyclic compounds containing at least one group of the type:

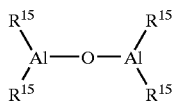

wherein the $R^{15}$ substituents, which may be the same or different, are described above.

In particular, alumoxanes of the formula:

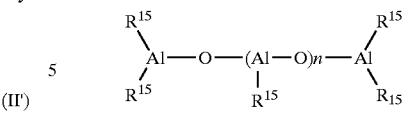

can be used in the case of linear compounds, wherein n is 0 or an integer from 1 to 40 and the $R^{15}$ substituents are defined as above, or alumoxanes of the formula:

can be used in the case of cyclic compounds, wherein n is an integer from 2 to 40 and the $R^{15}$ substituents are defined as above.

Examples of alumoxanes suitable for use according to the present invention are methylalumoxane (MAO), tetra-(isobutyl)alumoxane (TIBAO), tetra-(2,4,4-trimethyl-pentyl)alumoxane (TIOAO), tetra-(2,3-dimethylbutyl)alumoxane (TDMBAO) and tetra-(2,3,3-trimethylbutyl)alumoxane (TTMBAO).

Particularly interesting cocatalysts are those disclosed in WO 99/21899 and in PCT/EP00/09111 in which the alkyl and aryl groups have specific branched patterns.

Non-limiting examples of aluminium compounds according to said PCT applications are: tris(2,3,3-trimethyl-butyl)aluminium, tris(2,3-dimethyl-hexyl)aluminium, tris(2,3-dimethyl-butyl)aluminium, tris(2,3-dimethyl-pentyl)aluminium, tris(2,3-dimethyl-heptyl)aluminium, tris(2-methyl-3-ethyl-pentyl)aluminium, tris(2-methyl-3-ethyl-hexyl)aluminium, tris(2-methyl-3-ethyl-heptyl)aluminium, tris(2-methyl-3-propyl-hexyl)aluminium, tris(2-ethyl-3-methyl-butyl)aluminium, tris(2-ethyl-3-methyl-pentyl)aluminium, tris(2,3-diethyl-pentyl)aluminium, tris(2-propyl-3-methyl-butyl)aluminium, tris(2-isopropyl-3-methyl-butyl)aluminium, tris(2-isobutyl-3-methyl-pentyl)aluminium, tris(2,3,3-trimethyl-pentyl)aluminium, tris(2,3,3-trimethyl-hexyl)aluminium, tris(2-ethyl-3,3-dimethyl-butyl)aluminium, tris(2-ethyl-3,3-dimethyl-pentyl)aluminium, tris(2-isopropyl-3,3-dimethyl-butyl)aluminium, tris(2-trimethylsilyl-propyl)aluminium, tris(2-methyl-3-phenyl-butyl)aluminium, tris(2-ethyl-3-phenyl-butyl)aluminium, tris(2,3-dimethyl-3-phenyl-butyl)aluminium, tris(2-phenyl-propyl)aluminium, tris[2-(4-fluoro-phenyl)-propyl]aluminium, tris[2-(4-chloro-phenyl)-propyl]aluminium, tris[2-(3-isopropyl-phenyl)-propyl]aluminium, tris(2-phenyl-butyl)aluminium, tris(3-methyl-2-phenyl-butyl)aluminium, tris(2-phenyl-pentyl)aluminium, tris[2-(pentafluorophenyl)-propyl]aluminium, tris[2,2-diphenyl-ethyl]aluminium and tris[2-phenyl-2-methyl-propyl] aluminium, as well as the corresponding compounds wherein one of the hydrocarbyl groups is replaced by an hydrogen atom, and those wherein one or two of the hydrocarbyl groups are replaced by an isobutyl group.

Amongst the above aluminium compounds, trimethylaluminium (TMA), triisobutylaluminium (TIBAL), tris(2,4,4-trimethyl-pentyl)aluminium (TIOA), tris(2,3-dimethylbutyl)aluminium (TDMBA) and tris(2,3,3-trimethylbutyl)aluminium (TTMBA) are preferred.

The molar ratio between the aluminium and the metal of the metallocene compound is in general comprised between 10:1 and 20000:1, and preferably between 100:1 and 5000:1.

Non-limiting examples of compounds able to form an alkylmetallocene cation are compounds of formula $D^+E^-$, wherein $D^+$ is a Brønsted acid, able to give a proton and to react irreversibly with a substituent X of the metallocene of formula (I) and $E^-$ is a compatible anion, which is able to stabilize the active catalytic species originating from the reaction of the two compounds, and which is sufficiently labile to be able to be removed by an olefinic monomer. Preferably, the anion $E^-$ consists of one or more boron atoms. More preferably, the anion $E^-$ is an anion of the formula $BAr_4^{(-)}$, wherein the substituents Ar which can be identical or different are aryl radicals such as phenyl, pentafluorophenyl or bis(trifluoromethyl)phenyl. Tetrakis-pentafluorophenyl borate is particularly preferred. Moreover, compounds of the formula $BAr_3$ can conveniently be used. Compounds of this type are described, for example, in the published International patent application WO 92/00333, the content of which is incorporated in the present description.

The catalysts of the present invention can also be used on supports. This is achieved by depositing the metallocene compound (A) or the product of the reaction thereof with the component (B), or the component (B) and then the metallocene compound (A) on supports such as, for example, silica, alumina, magnesium halides, styrene/divinylbenzene copolymers, polyethylene or polypropylene.

A suitable class of supports, which can be used, is constituted by porous organic supports functionalized with groups having active hydrogen atoms. Particularly suitable are those in which the organic support is a partially crosslinked styrene polymer. Supports of this type are disclosed in European application EP-A-0 633 272.

Another class of inert supports particularly suitable for use according to the invention is that of the olefin, particularly propylene, porous prepolymers described in International application WO 95/26369.

A further suitable class of inert supports for use according to the invention is that of the porous magnesium halides such as those described in International application WO 95/32995.

The solid compound thus obtained, in combination with the further addition of the alkylaluminium compound either as such or prereacted with water if necessary, can be usefully employed in the gas-phase polymerization.

The process for the polymerization of olefins according to the invention can be carried out in the liquid phase in the presence or absence of an inert hydrocarbon solvent, or in the gas phase. The hydrocarbon solvent can be either aromatic such as toluene, or aliphatic such as propane, hexane, heptane, isobutane or cyclohexane.

The polymerization temperature is generally comprised between $-100°$ C. and $+200°$ C. and, particularly between $10°$ C. and $+90°$ C. The polymerization pressure is generally comprised between 0,5 and 100 bar.

The lower the polymerization temperature, the higher are the resulting molecular weights of the polymers obtained.

The polymerization yields depend on the purity of the metallocene compound of the catalyst. The metallocene compounds obtained by the process of the invention can therefore be used as such or can be subjected to purification treatments.

The components of the catalyst can be brought into contact with each other before the polymerization. The pre-contact concentrations are generally between 1 and $10^{-8}$ mol/l for the metallocene component (A), while they are generally between 10 and $10^{-8}$ mol/l for the component (B).

The pre-contact is generally effected in the presence of a hydrocarbon solvent and, if appropriate, of small quantities of monomer.

According to another aspect of the present invention a process is provided for the preparation of a ligand of formula (V):

$$SIR^1R^2Q'L' \qquad (V)$$

wherein

Q' is a moiety of the general formula (VI):

(VI)

and its double bond isomers, wherein A, B, $R^3$ and $R^4$ are defined as described above;

L' is a moiety of the general formula (VII):

(VII)

and its double bond isomers, wherein $R^1, R^2 R^6, R^7, R^8$ and $R^9$ are defined as described above, comprising the following steps:
  i) treating the compound of formula (VIII) with at least one equivalent of a base selected from the group consisting of metallic sodium and potassium, sodium and potassium hydroxide and an organolithium compound;

(VIII)

wherein the rings containing A and B have a double bond in the allowed position having an aromatic character; A, B, $R^3$ and $R^4$ are defined as above;
  ii) contacting the corresponding anionic compound obtained under i) with a compound of general formula (IX):

$$YL'SiR^1R^2 \qquad (IX)$$

wherein L', $R^1, R^2$ have the meaning described above and Y is a halogen atom selected from the group consisting of fluoride, chloride, bromide and iodide;

An alternative process for preparing the ligand of formula (V) comprises the following steps:

i) treating the compound of formula (VIII) with at least one equivalent of a base selected from the group consisting of metallic sodium and potassium, sodium and potassium hydroxide and an organolithium compound;

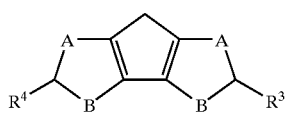

(VIII)

wherein the rings containing A and B have a double bond in the allowed position having an aromatic character, A, B, $R^3$ and $R^4$ are defined as above;

ii) contacting the corresponding anionic compound obtained under i) with a compound of general formula (X):

$$Y_2SiR^1R^2 \qquad (X)$$

wherein L', R', $R^2$ have the meaning described above and Y is a halogen atom selected from the group consisting of fluoride, chloride, bromide and iodide;

iii) contacting the product obtained in step ii) with a compound of formula (XI)

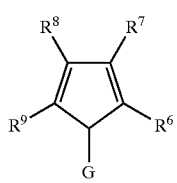

(XI)

wherein $R^6$, $R^7$, $R^8$ and $R^9$ are described above and G is, selected from sodium, potassium and lithium, preferably G is lithium.

The synthesis of the above bridged ligand is preferably carried out by adding a solution of an organolithium compound in an apolar solvent to a solution containing the compounds of formulae (VII) and (IX) respectively in an aprotic polar solvent. The bridged ligand can be separated by conventional general known procedures.

Not limitating examples of aprotic polar solvents which can be used in the above process are tetrahydrofurane, dimethoxyethane, diethylether, toluene and dichloromethane. Not limiting examples of apolar solvents suitable for the above process are pentane, hexane and benzene.

During the whole process, the temperature is preferably kept between −80° C. and 100° C., and more preferably between −20° C. and 40° C.

The compound of formula (VII) is an important intermediate for preparing the ligand of formula (V). When both $R^3$ and $R^4$ are hydrogen the corresponding compound of formula (VII) is obtained according to WO 98/22486.

In the case that B is a $CR^5$ group and preferably $R^4$ and $R^5$ the which may be the same or different from each other, are selected from a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13 or 15–17 of the Periodic Table of the Elements, the corresponding compound of formula (VII) can be obtained with a process comprising the following steps:

i) treating a compound of formula (XII):

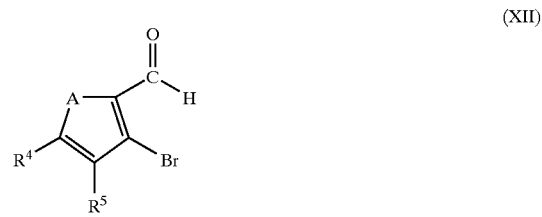

(XII)

wherein A is sulfur or oxygen, with a compound of formula (XIII):

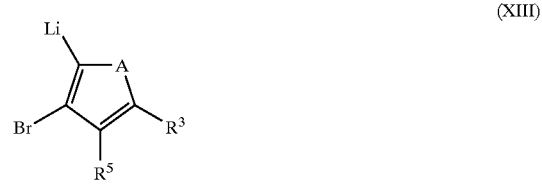

(XIII)

wherein A is sulfur or oxygen, ii) contacting the thus obtained product with a reducing agent in a molar ratio between said reducing agent and the product obtained under i) of at least 1;

iii) contacting the product obtained under ii) with a compound selected from an organolithium compound, sodium and potassium in a molar ratio between said compound and the product obtained in step ii) of equal to or greater than 2;

iv) treating the thus obtained product with an agent selected from the group consisting of copper chloride, iodine and Mg/Pd., in order to obtain a compound of general formula (XIV):

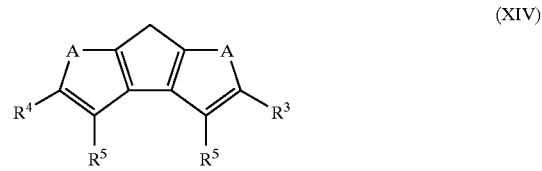

(XIV)

When B is sulfur or oxygen and A is a $CR^5$ group and preferably $R^4$ and $R^3$ the which may be the same or different from each other, are selected from a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13 or 15–17 of the Periodic Table of the Elements, the corresponding compound of formula (VI) can be obtained according to the process comprising the following steps:

i) contacting a compound of formula (XV):

(XV)

wherein B is sulfur or oxygen, with a compound of formula (XVI):

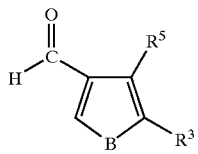

(XVI)

wherein B is sulfur or oxygen,
and subsequently treating with a neutralization agent;
ii) treating the thus obtained product with a reducing agent in a molar ratio between said reducing agent and the compound obtained under i) of at least 1;
iii) contacting the thus obtained product with a mixture of an organolithium compound and tetramethylethylenediamine (TMEDA) in a molar ratio between said mixture and the product obtained under ii) of at least 2,
iv) contacting the thus obtained product with an agent selected from the group consisting of copper chloride, iodine and Mg/Pd., in order to obtain a compound of formula (XVII):

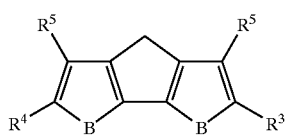

(XVII)

An alternative process for preparing the compound of formula (VII) when A is S or O and preferably $R^4$ and $R^3$ the which may be the same or different from each other, are selected from a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl, $C_7$–$C_{20}$-arylalkyl radical, optionally containing heteroatoms belonging to groups 13 or 15–17 of the Periodic Table of the Elements, comprises the following steps:
i) contacting an equimolar mixture of compounds of formulae (XVIII) and (XIX):

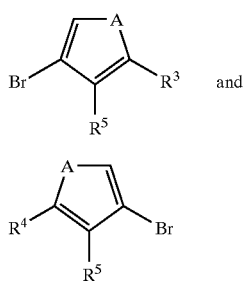

XVIII and

XIX wherein A are sulfur or oxygen,
with a Lewis acid or a mixture of a Lewis acid and a protonic acid;
ii) treating the thus obtained product with $CH_2O$ in a molar ratio between said mixture and $CH_2O$ of a range between 10:1 and 1:10;
iii) contacting the thus obtained product with a compound selected from an organolithium compound, sodium and potassium;
iv) contacting the thus obtained product with an agent selected from the group consisting of copper chloride, iodine and Mg/Pd., in order to obtain a compound of general formula (XIV)

The Lewis acid used in the above processes is preferably selected from zinc dichloride, cadmium dichloride, mercurium dichloride, tin tetrachloride, trifluoroborane, zirconium tetrachloride, titanium tetrachloride. Most preferably, the Lewis acid is zinc dichloride.

In the above processes the agent used is preferably copper chloride; preferably the reducing agent is a mixture of $AlCl_3/LiAlH_4$; the organolithium compound used above is preferably butyllithium.

Compounds of formula (VII) can suitable be used as intermediates for the preparation of metallocenes of formula (I).

Thus, it is a further aspect of the present invention a process for the preparation of a metallocene of the general formula (I):

$$SiR^1R^2QLMX_p \qquad (I)$$

wherein Q, L, $R^1$, $R^2$, M, X and p have the meaning as defined above, comprising the following steps:
a) contacting a compound of the formula (VI):

$$SiR^1R^2Q'L' \qquad (VI)$$

wherein
Q', L, $R^1$ and $R^2$ are defined as mentioned above with a base, wherein the ratio between said base and the compound of formula (VI) is at least 2,
b) contacting the obtained product with a compound of formula $MX_{p+2}$, wherein M and X are defined as stated above and p is an integer equal to the oxidation state of the metal minus 2.

Preferably, the base is buthyllithium.

Preferably $MX_{p+2}$ is selected from $ZrCl_4$, $TiCl_4$, $HfCl_4$ and the $C_1$–$C_6$-alkyl analogues thereof. The reaction is carried out in an inert solvent such as toluene, tetrahydrofurane, benzene, diethyl ether, hexane and the like at a temperature range from –78° C. to 100° C.

In the case in which at least one substituent X in the metallocene compound of the formula (I) is different from halogen an alternative process for preparing it, consists in preparing the dihalogen derivative i.e. the complex wherein both X are halogen and then substituting the halogen atom with the appropriate X group by means of generally applied methods. For example, if the desired substituents X are alkyl groups, the metallocenes can be made to react with alkylmagnesium halides (Grignard reagents) or with alkyllithium compounds. General methods for substituting X by substituents other than halogen such as sulfur, phosphorus, oxygen, etc. are described in Chem. Rev. 1994, 94, 1661–1717, and the therein cited references.

In the process according to the present invention ethylene homopolymers are obtainable having a remarkably high molecular weight. In fact, with the process of the present invention it is possible to obtain ethylene polymers having intrinsic viscosity values (I.V.) as high as 5.0 dl/g and even higher.

In the copolymers obtainable with the process of the invention, the molar content of ethylene derived units is generally higher than 40%, and preferably it is comprised between 50% and 99%, and most preferably it is comprised between 80% and 98%.

The molar content of alpha-olefin derived units is preferably comprised between 0% and 60% and, more preferably, between 1% and 50%, and most preferably between 2% and 20%.

Non-limiting examples of alpha-olefins which can be used as alpha-olefins in the process of the invention are propylene, 1-butene, 1-pentene, 4-methyl-1-pentene, 1-hexene, 1-octene, 4,6-dimethyl-1-heptene, 1-decene, 1-dodecene, 1-tetradecene, 1-hexadecene, 1-octadecene, 1-eicosene and allylcyclohexane.

Non-limiting examples of cycloolefins that can be used as comonomers in the process of the present invention are cyclopentene, cyclohexene and norbornene.

The copolymers according to the invention can also contain units derived from polyenes. The content of polyene derived units, if any, is preferably comprised between 0% and 30% by mol and, more preferably between 0 mol % and 20 mol %.

The polyenes that can be used as comonomers in the copolymers according to the present invention are included in the following classes:

non-conjugated diolefins able to cyclopolymerize such as, for example, 1,5-hexadiene, 1–6-heptadiene, 2-methyl-1,5-hexadiene;

dienes capable of giving unsaturated monomeric units, in particular conjugated dienes such as, for example, butadiene and isoprene, and linear non-conjugated dienes, such as, for example, trans 1,4-hexadiene, cis 1,4-hexadiene, 6-methyl-1,5-heptadiene, 3,7-dimethyl-1,6-octadiene, 11-methyl-1,10-dodecadiene, and cyclic non-conjugated dienes such as 5-ethylidene-2-norbornene The analysis of the distribution of the comonomer units in the copolymers of the invention has been carried out by means of $^{13}$C-NMR spectroscopy. The assignments were carried out as described by Randall in Macromol. Chem. Phys. 29, 201, 1989. The distribution of triads, in the case of ethylene/1-hexene, are calculated by means of the following relationships:

$$HHH=T_{\beta\beta} \quad EHE=T_{\delta\delta} \quad HHE=T_{\beta\delta} \quad HEH=S_{\beta\beta} \quad HEE=S_{\beta\delta} \quad EEE=0.5(S_{\delta\delta}+0.5S_{\gamma\delta})$$

wherein EHE, HHE and HHH represent the sequence ethylene/1-hexene/ethylene, 1-hexene/1-hexene/ethylene and 1-hexene/1-hexene/1-hexene respectively in the copolymer. For the NMR nomenclature, see J. Carman, R. A. Harrington, C. E. Wilkes, Macromolecules, 10, 537 (1977). The sum of the triads is normalized to 100. The higher the number of isolated 1-hexene units in the polymeric chain, the more the values of the ratio EHE/(EHE+HHE+HHH) become closer to the unit.

The number of 1-hexene sequences is generally a function of the amount of 1-hexene units present in the chain.

The Tables 2 and 3 refer to ethylene/1-hexene copolymers obtained with a process according to the present invention.

In particular, in Table 3 there are reported the ratios EHE/(EHE+HHE+HHH) as a function of the molar percentage of 1-hexene in the chain for ethylene/1-hexene copolymers obtained with a process according to the present invention, in the presence of the metallocene compounds reported above.

In the case of ethylene/1-hexene, the reactivity ratio $r_1$ and the product of the reactivity ratios $r_1 \cdot r_2$ are calculated according to the following formulae as described in J. Uozomi, K. Soga, Mak. Chemie, 193, 823, (1992):

$$r_1=2[EE]/[EH]X$$

$$r_1 \cdot r_2=4[EE][HH]/[EH]^2$$

wherein X=[E]/[H] monomer molar ratio in the polymerization bath.

The process of the present invention can also be carried out in a gas phase for the polymerization of ethylene with alpha-olefins such as propylene, 1-butene, 1-pentene, 4-methyl-1-pentene, 1-hexene, 1-octene, 4,6-dimethyl-1-heptene, 1-decene, 1-dodecene, 1-tetradecene, 1-hexadecene, 1-octadecene, 1-eicosene and allylcyclohexane.

Particularly good results are obtained in the gas phase when the polymerization of ethylene is carried out with 1-octene.

The process of the present invention can be also used as last step of a multistep process described in EP 720629 and EP 742801. In this process a polymer previously prepared with a different catalyst system is impregnated with the olefin polymerization catalyst system herein and then ethylene and one or more olefins are polymerized according to the process of the present invention. The polymer of the first steps range from 10 to 70% of the total polymer obtained in the multistep process, preferably from 10 to 6o %, more preferably 20 to 50%.

The metallocene compounds of the general formula (I) as defined above are particularly useful for the preparation of copolymer of ethylene with propylene and optionally a polyene.

Therefore, according to another aspect the present invention relates to a copolymer of ethylene with propylene and a polyene, having a content of ethylene derived units comprised between about 35 mol % and 85 mol %, a content of $C_4$–$C_{10}$-alpha-olefin derived units comprised between about 10 mol % and 60 mol % and a content of a $C_4$–$C_{30}$-polyene derived units comprised between about 0.1 mol % and 5 mol %, and having the following characteristics:

(A) the % by mole content of the α-olefin in the copolymer (%α) and the ratio EαE/(EαE+ααE+ααα), wherein EαE, ααE and ααα represent the sequences ethylene/α-olefin/ethylene, α-olefin/α-olefin/ethylene and α-olefin/α-olefin/α-olefin respectively in the copolymer, satisfy the following relationship:

$$0.01\%\alpha+E\alpha E/(E\alpha E+\alpha\alpha E+\alpha\alpha\alpha) \geq 1$$

(B) less than 2% of the $CH_2$ groups in the polymeric chain are sequences $(CH_2)_n$, wherein n is an even number.

The molar content of the ethylene derived units is preferably comprised between about 50% and 85% and, more preferably, between about 60% and 80%.

The molar content of the α-olefin derived units is preferably comprised between about 15% and 50% and, more preferably, between about 20% and 40%.

The molar content of the polyene derived units is preferably comprised between about 0.1% and 4% and, more preferably, between about 0.1% and 3%.

The polyenes that can be used as comonomers in the copolymers according to the present invention are comprised in the following classes:

non-conjugated diolefins able to cyclopolymerize such as, for example, 1,5-hexadiene, 1–6-heptadiene, 2-methyl-1,5-hexadiene;

dienes capable of giving unsaturated monomeric units, in particular conjugated dienes such as, for example, butadiene and isoprene, and linear non-conjugated dienes, such as, for example, trans 1,4-hexadiene, cis 1,4-hexadiene, 6-methyl-1,5-heptadiene, 3,7-dimethyl-1,6-octadiene, 11-methyl-1,10-dodecadiene, and cyclic non-conjugated dienes such as 5-ethylidene-2-norbornene A preferred polyene for use in the copolymers of the invention is 5-ethylidene-2-norbornene (ENB).

Non-limiting examples of cycloolefins that can be used as comonomers in the process of the invention are cyclopentene, cyclohexene and norbornene.

The copolymers according to the invention can also contain units derived from polyenes. The content of polyene derived units, if any, is preferably comprised between 0% and 4% and, more preferably between 0% and 3%.

In the case of polyenes other than non-conjugated alpha-omega-diolefins hating 6 or more carbon atoms, these are preferably used in quantities of between 0 and 3 mol % as a second alpha-olefin comonomer.

A particular interesting embodiment of the present invention is constituted of copolymers of ethylene with propylene, 1-hexene or higher alpha-olefins.

The analysis of the distribution of the comonomer units in the copolymers of the invention has been carried out by means of $^{13}$C-NMR spectroscopy. The assignments were carried out as described by M. Kagugo et al. in "Macromolecules, 15, 1150–1152 (1982)". The distribution of triads, in the case of ethylene/propylene, are calculated by the following relationship:

$$EPE=T_{\delta\delta} PPE=T_{\beta\delta} PPP=T_{\beta\beta} PEE=S_{\alpha\delta} PEP=S_{\beta\beta} EEE=0.5(S_{\delta\delta}+0.5S_{\gamma\delta})$$

wherein EPE, PPE, PPP, PEE, PEP and EEE represent the sequences ethylene/propylene/ethylene, propylene/propylene/ethylene, propylene/propylene/propylene, propylene/ethylene/ethylene, propylene/ethylene/propylene and ethylene/ethylene/ethylene respectively in the copolymer. The sum of the triads is normalized to 100. In the case of terpolymers the molar composition is calculated from $^{1}$H-NMR spectra. EPE, PPE, PPP, PEE, PEP and EEE triads are calculated from $^{13}$C-NMR spectra as previously described for the copolymers, neglecting the presence of the termonomer. The higher the number of isolated propylenic units in the polymeric chain, the more the values of the ratio EPE/(EPE+PPE+PPP) become closer to the unity. Generally it is a function of the amount of propylenic units present in the chain.

The Tables 4 and 5 refer to ethylene/propylene copolymers obtained with a process according to the present invention.

In particular, the percentage molar content of propylene in the copolymer of the present invention (% P) and the ratio EPE/(EPE+PPE+PPP) satisfy the following relationship:

$$0.01\% \; P+EPE/(EPE+PPE+PPP) \geq 1$$

preferably:

$$0.008\% \; P+EPE/(EPE+PPE+PPP) \geq 1$$

more preferably:

$$0.006\% \; P+EPE/(EPE+PPE+PPP) \geq 1.$$

In particular, in Table 5 there are reported the ratios EPE/(EPE+PPE+PPP) as a function of the molar percentage of propylene in the chain for ethylene/propylene copolymers obtained with a process according to the present invention, in the presence of the metallocene compounds reported above.

In the copolymers obtained with a process according to the present invention, the product of the reactivity ratios $r_1 \cdot r_2$, wherein $r_1$ is the reactivity ratio of propylene and $r_2$ that of ethylene, calculated according to the following formula:

$$r_1 r_2 = 1 + f(\chi+1) - (f+1)(\chi+1)^{1/2}$$

wherein
  f=ratio between moles of ethylene units and moles of propylene units in the copolymer, and
  $\chi$=(PPP+PPE)/EPE,
  appears to be extremely low. In particular, it is generally lower than 0.2, preferably lower than 0.1 and, more preferably, lower than 0.08.

The propylene units in the copolymer obtained according to the present invention appear to be highly regioregular. In fact, from the $^{13}$C-NMR analysis no signals are revealed as deriving from the $(CH_2)_n$ sequence where n is an even number. Preferably, less than 1% of the $CH_2$ groups in the chain are contained in a $(CH_2)_n$ sequence, where n is an even number.

The copolymers of the present invention have intrinsic viscosity values (I.V.) generally higher than 0.5 dl/g and preferably higher than 1.0 dl/g. The intrinsic viscosity can reach values of 4.0 dl/g and even higher.

The molecular weight of the polymers can also be modified by varying the type or the concentration of the catalyst components, or by using molecular weight regulators such as, for example, hydrogen.

Generally, the polymers of the present invention are endowed with a narrow molecular weight distribution. The molecular weight distribution is represented by the ratio $M_w/M_n$ which, for the polymers of the present invention, when the metallocene used is a pure isomer, is generally lower than 4, preferably lower than 3.5 and, more preferably, lower than 3.

The molecular weight distribution can be varied by using mixtures of different metallocene compounds or by carrying out the polymerization in several stages at different polymerization temperatures and/or different concentrations of the molecular weight regulators.

The polymers of the invention are generally soluble in common solvents, such as, for instance, chloroform, hexane, heptane, toluene and xylene.

Another object of the present invention is an elastomeric copolymer obtainable by subjecting a copolymer according to the present invention to a vulcanization process.

The copolymers of the present invention may be vulcanized using the known techniques and methods for the EPR and EPDM rubbers, operating, for example, in the presence of peroxides or sulfur. Rubbers are obtained having valuable elastomeric properties.

Still another object of the present invention is a shaped article obtained from the above said elastomeric copolymer.

The rubbers obtained from the copolymers of the present invention are transformable into shaped articles by the normal thermoplastic material processing, such as molding, extrusion, injection, etc. The relative shaped articles are endowed with interesting elastomeric properties and find uses in all typical applications of the ethylene-based elastomers, such as EPR and EPDM. In particular, the products obtained from the copolymers of the present invention which have a high content of ethylene units, can be advantageously used as coatings for wires and cables.

The following examples are given for illustrative purposes and are not intended to limit the scope and spirit of the invention.

EXAMPLES

General Procedures and Characterisations
  The following abbreviations are used:
  THF=tetrahydrofuran
  Et$_2$O=ethyl ether
  NaOEt=sodium ethoxide 'BuOK=potassium tert-butoxide
DMSO=dimethyl sulfoxide
DMF=N,N-dimethyl sulfoxide
BuLi=butyllithium All operations were performed under nitrogen by using conventional Schlenk-line techniques. Solvents were distilled from blue Na-benzophenone ketyl (Et$_2$O), CaH$_2$ (CH$_2$Cl$_2$), or Al-iBu$_3$ (hydrocarbons), and stored under nitrogen. BuLi (Aldrich) was used as received.

The $^1$H-NMR analyses of the metallocenes were carried out on a Varian VXR-400 spectrometer (CD$_2$Cl$_2$, referenced against the middle peak of the triplet of residual CHDCl$_2$ at 5.35 ppm). All NMR solvents were dried over P$_2$O$_5$ and distilled before use. Preparation of the samples was carried out under nitrogen using standard inert atmosphere techniques.

The $^{13}$C-NMR and $^1$H-NMR analyses of the polymers were carried out on a Bruker DPX 400 spectrometer operating at 400.13 MHz and 100.61 MHz respectively and were analyzed at 120° C. The powder polymer samples were dissolved in 1,1,2,2-tetrachloro-1,2-dideuteroethane (C$_2$D$_2$Cl$_4$) to give an 8% (wt./vol.) concentration. About 13000 transients were acquired with a 75° pulse and 15 seconds of delay between pulses.

Intrinsic Viscosity

The determinations were carried out in a tetrahydronaphthalene (THN) solution obtained by dissolving the polymer at 135° C. for 1 hour.

The melting points of the polymers (Tm) were measured by Differential Scanning Calorimetry (D.S.C.) on an t DSC Mettler instrumen, according to the following method. About 10 mg of a sample obtained from the polymerization were cooled to −25° C. and thereafter heated at 200° C. with a scanning speed corresponding to 20° C. minute. The sample was kept at 200° C. for 5 minutes and thereafter cooled to 0° C. with a scanning speed corresponding to 20° C./minute. After standing for 5 minutes at 0° C., the sample was heated to 200° C. at a rate of 10° C./min. In this second heating run, the peak temperature was taken as melting temperature (T$_m$) and the area as global melting hentalpy (ΔH$_f$).

Size exclusion chromatography (SEC):
The analysis were performed by using a "WATERS 200" GPC, working at 135° C. with 1,2-dichlorobenzene (stabilized with BHT, 0.1 wt. %).

Preparation of the Ligand Precursor
Synthesis of 2,5-dimethyl-cyclopentadienyl-[1,2-b:4,3-b'] dithiophene

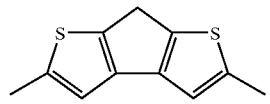

Preparation of 2-Methyl-4-thiophene-aldehyde 44.26 g of 2-methyl-4-bromo-thiophene (0.25 mol) was dissolved in 300 ml ether and treated dropwise with 164 ml 1.6M BuLi (0.26 mol) at −70° C. The resulting solution kept under stirring at −60-−70° C. in 30 min and then was treated with 27.4 g dimethylformamide (0.37 mol) in 100 ml ether. The mixture was allowed to warm to r.t., then neutralized by 10% aq. NH$_4$Cl, washed with 10% H$_3$PO$_4$ and finally with water up to neutral pH. The organic phase was collected, evaporated off and distilled at 110°/10 mmHg. Yield 22.3 g (71%). The title compound was analyzed by $^1$H-NMR spectroscopy.

Preparation of Bis(2-methyl-4-thienyl)methane 31.3 g of 2-methyl-4-bromo-thiophene (0.177 mol) was dissolved in 150 ml ether and treated dropwise with 113 ml 1.6M BuLi (0.1 mol) at −70° C. The resulting solution kept under stirring at −60 to −70° C. for 30 min and then was treated with 22.3 g 2-methyl-4-thiophene-aldehyd (0.177 mol) in 100 ml ether. The mixture was allowed to warm to r.t., then neutralized by 10% aq. NH$_4$Cl and washed with water. The organic phase was collected and evaporated off. The suspension of 10 g LiAlH$_4$ (0.266 mol) in 100 ml ether was treated dropwise with the solution of 35.5 g AlCl$_3$ (0.266 mol) in 100 ml ether. The resulting mixture was treated with the solution of the compound obtained in the previous reaction in 100 ml ether. The mixture refluxed for additional 1 h, cooled up to r.t. and treated with 100 ml ethyl acetic ester. Then the mixture was treated with 300 ml H$_2$O and 300 ml ether. Organic phase was collected, washed with water, dried over MgSO4 and evaporated off. The residue was distilled at 90–110/0.5 mmHg. Yield 23.2 g (63%). The title compound was analyzed by $^1$H-NMR spectroscopy.

Preparation of 2,5-dimethyl-cyclopentadienyl-[1,2-b:4,3-b'] dithiophene 1.04 g of bis(5-methyl-3-thienyl)methane (5 mmol) was dissolved in 30 ml ether and treated at −70° C. with 9 ml 1.6M BuLi (15 mmol) and 1.74 g TMEDA (15 mmol). The resulting mixture was allowed to warm to r.t., stirred in 1 h, then cooled to −70° C. and treated with 2.7 g CuCl$_2$ (20 mmol). The resulting mixture was allowed to warm to r.t. and treated with 30 ml water. The organic phase was collected, and passed through the column with silica gel. The resulting solution was evaporated off to give 0.34 g of the product (34%). The title compound was analyzed by $^1$H-NMR spectroscopy.

Preparation of the Bridged Ligands

Example 1

Synthesis of (2,5-dimethyl-7H-thieno[1,2-b:4,3-b'] cyclopenta[b]thiophene-7-yl)(9H-9-fluorenyl) dimethylsilane A solution of 1.03 g (5 mmol) of 2,5-dimethyl-cyclopentadiene-[1,2-b:4,3-b']-dithiophene in 20 ml ether was treated at −70° C. with 3.13 ml of 1.6M BuLi (5 mmol). The resulting mixture was stirred in additional 30 min at 0° C., cooled again to −70° C. and then was treated with 1.29 g (5 mmol) dimethyl(9H-9-fluorenyl)chlorosilane in 10 ml ether. The mixture was allowed to warm to r.t. then was treated with saturated aqueous solution of NH$_4$Cl. The organic phase was isolated, the solvent was removed and the residue was recrystallyzed from hexane. Yield 1.28 g (60%). The title compound was analyzed by $^1$H-NMR and $^{13}$C-NMR spectroscopy.

Example 2

Synthesis of [2,7-di(tert-butyl)-9H-9-fluorenyl](2,5-dimethyl-7H-thieno[3'2':3,4]cyclopenta[b]thiophene-7-yl) dimethylsilane A solution of 1.03 g (5 mmol) of 2,5-dimethyl-cyclopentadiene-[1,2-b:4,3-b']-dithiophene in 20 ml ether was treated at −70° C. with 3.13 ml of 1.6M BuLi (5 mmol). The resulting mixture was stirred in additional 30 min at 0° C., cooled again to −70° C. and then was treated with 1.86 g (5 mmol) dimethyl(2,7-di-tert-butyl)-(9H-9-fluorenyl) chlorosilane in 10 ml ether. The mixture was allowed to warm to r.t., and then treated with saturated aqueous solution of NH$_4$Cl. The organic phase was isolated, the solvent was removed and the residue was recrystallyzed from hexane. Yield 1.44 g (58%). The title compound was analyzed by $^1$H-NMR and $^{13}$C-NMR spectroscopy.

Example 3
Synthesis of di(2,5-dimethyl-7H-thieno[1,2-b:4,3-b']cyclopenta[b]thiophen-7-yl)dimethylsilane A solution of 1.03 g (5 mmol) of 2,5-dimethyl-cyclopentadiene-[1,2-b:4,3-b']-dithiophene in 20 ml ether was treated at −70° C. with 3.13 ml of 1.6M BuLi (5 mmol). The resulting mixture was stirred in additional 30 min at 0° C., cooled again to −70° C. and then was treated with 0.32 g (2.5 mmol) dimethyl-dichlorosilane in 10 ml ether. The mixture was allowed to warm to r.t. then was treated with saturated aqueous solution of $NH_4Cl$. The organic phase was isolated, the solvent was removed and the residue was recrystallyzed from hexane. Yield 1.66 (71%). The title compound was analyzed by $^1$H-NMR spectroscopy.

Example 4
Synthesis of 2,5-dimethyl-7H-thieno[1,2-b:4,3-b']cyclopenta[b]thiophen-7-yl)(dimethyl)(2,3,4,5-tetramethyl-2,4-cyclopentadienyl)silane A solution of 1.03 g (5 mmol) of 2,5-dimethyl-cyclopentadiene-[1,2-b:4,3-b']-dithiophene in 20 ml ether was treated at −70° C. with 3.13 ml of 1.6M BuLi (5 mmol). The resulting mixture was stirred in additional 30 min at 0° C., cooled again to −70° C. and then was treated with 1.07 g (5 mmol) (2,3,4,5-tetramethyl-2,4-cyclopentadienyl)dimethylchlorosilane in 10 ml ether. The mixture was allowed to warm to r.t., the product starts to precipitate. It was filtered off, washed with water and dried. Yield 0.84 g (50%).

The title compound was analyzed by $^1$H-NMR spectroscopy.

Preparation of the Metallocenes
Preparation of dimethylsilandiylbis(fluorenyl)zirconium dichloride [$Me_2Si(Flu)_2ZrCl_2$]

It was carried out as described on page 7 of EP-A-0 632 066.

Preparation of 2,5-dimethyl-7H-thieno[1,2-b:4,3-b']cyclopenta[b]thiophen-7-yl)(dimethyl)(2,3,4,5-tetramethyl-2,4-cyclopentadienyl)silanedichlorozirconium [$Me_2Si(Me_4Cp)(7-MeTh_2-Cp)ZrCl_2$]

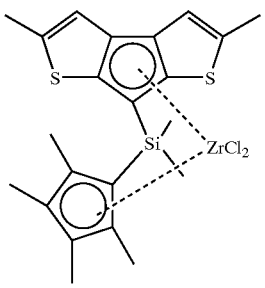

A suspension of 0.8 g (2.1 mmol) of 2,5-dimethyl-7-thieno[3',2':3,4]cyclopenta[b]thiophen-7-yl)(dimethyl)(2,3,4,5-tetramethyl-2,4-cyclopentadienyl)silane in 20 ml ether was treated with 2.6 ml (4.2 mmol) 1.6M BuLi at −70° C. The mixture was allowed to warm to r.t, the yellowish dilithium salt precipitates. The salt was washed twice with ether and then was treated at −50° C. with the suspension of 0.48 g (2.1 mmol) $ZrCl_4$ in 20 ml ether. The reaction mixture was stirred at reflux within 3 h, then the yellow precipitate was filtered off, washed twice with ether, dried and then recrystallyzed from $CH_2Cl_2$. Yield 1.02 g (90%). The title compound was analyzed by $^1$H-NMR and $^{13}$C-NMR spectroscopy.

Preparation of (2,5-dimethyl-7H-thieno[1,2-b:4,3-b']cyclopenta[b]thiophen-7-yl)(9H-9-fluorenyl)dimethylsilyldichlorozirconium [$Me_2Si(Flu)(7-MeTh_2–Cp)ZrCl_2$]

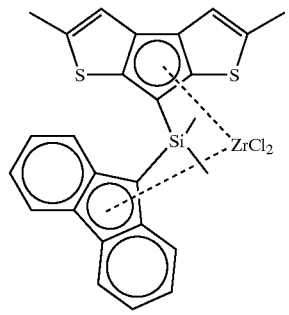

A suspension of 1.28 g (3.0 mmol) of (2,5-dimethyl-7H-thieno[3'2':3,4]cyclopenta[b]thiophene-7-yl)(9H-9-fluorenyl)dimethylsilane in 20 ml ether was treated with 3.75 ml (6.0 mmol) 1.6M BuLi at −70° C. The mixture was allowed to warm to r.t, the yellowish dilithium salt precipitates. The salt was washed twice with ether and dried. The salt so-obtained was suspended in 20 ml of $CH_2Cl_2$ at −70° C. and then was treated with 0.7 g (3 mmol) of $ZrCl_4$ at the same temperature. The reaction mixture was allowed to warm to r.t., then was stirred at reflux within 1 h. The red crystalline precipitate was filtered off, washed twice with $CH_2Cl_2$ and dried. Yield 1.31 g (90%).

Preparation of (2,5-dimethyl-7H-thieno[1,2-b:4,3-b']cyclopenta[b]thiophen-7-yl)(2,7-di(tert-butyl)9H-9-fluorenyl)dimethylsilyldichlorozirconium [$Me_2Si(2,7-tBu_2-Flu)(7-MeTh_2-Cp)ZrCl_2$]

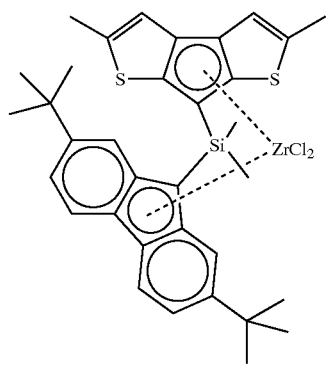

A suspension of 1.41 g (3.0 mmol) of [2,7-di(tert-butyl)-9H-9-fluorenyl](2,5-dimethyl-7H-thieno[3'2':3,4]cyclopenta[b]thiophene-7-yl)(9H-9-fluorenyl)dimethylsilane in 20 ml ether was treated with 3.75 ml (6.0 mmol) 1.6M BuLi at −70° C. The mixture was allowed to warm to r.t, the yellowish dilithium salt precipitates. The salt was washed twice with ether and dried. The salt so-obtained was suspended in 20 ml of $CH_2Cl_2$ at −70° C. and then was treated with 0.7 g (3 mmol) of $ZrCl_4$ at the same temperature. The reaction mixture was allowed to warm to r.t., then was stirred at reflux within 1 h. The red crystalline precipitate was filtered off, washed twice with $CH_2Cl_2$ and dried. Yield 1.76 g (90%). The desired compound was determined by $^1$H- and $^{13}$C-NMR spectroscopy.

Preparation of di-(2,5-dimethyl-7H-thieno[1,2-b:4,3-b']cyclopenta[b]thiophen-7-yl)dimethylsilyldichlorozirconium [Me₂Si(7-MeTh₂-Cp)₂ZrCl₂]

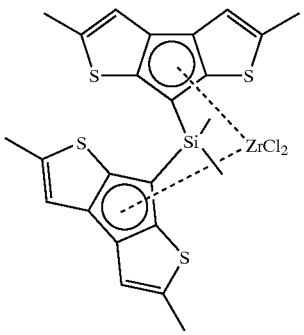

A suspension of 1.41 g (3.0 mmol) of (2,5-dimethyl-7H-thieno[3'2':3,4]cyclopenta[b]thiophene-7-yl)dimethylsilane in 20 ml ether was treated with 3.75 ml (6.0 mmol) 1.6M BuLi at −70° C. The mixture was allowed to warm to r.t. and then 0.7 g (3 mmol) of ZrCl₄ at the same temperature. The reaction mixture was stirred ar reflux within 3 h. The red precipitate was filtered off, washed twice with Ether and dried. Yield 1.47 g (80%). The desired compound was determined by ¹H- and ¹³C-NMR spectroscopy.

Polymerization
Methylalumoxane (MAO)

A commercial (Witco) 10% toluene solution was dried in vacuum until a solid, glassy material was obtained which was finely crushed and further treated in vacuum until all volatiles were removed (4–6 hours, 0.1 mmHg, 50° C.) to leave a white, free-flowing powder.

Tris(2,4,4-trimethyl-pentyl)aluminum (TIOA)

A commercial (Witco) sample was used diluted to a 1 M solution in the indicated solvent.

Preparation of TIOAO 5 ml of toluene and 3.15 mmol (3.45 ml) of TIOA solution (1 M in hexane) are introduced in a Schlenk tube. Then 1.75 mmol (31.5 μl) of H₂O are added, and the resultant solution is stirred for 10 minutes at room temperature.

Polymerization Examples 1 to 3
Ethylene polymerization in a Glass Autoclave

Ethylene polymerization under standard conditions was performed in a 200 ml glass autoclave, provided with magnetic stirrer, temperature indicator and feeding line for the ethylene. It was purified and fluxed with ethylene at 35° C. 140 ml of heptane were introduced at room temperature. The catalytic system was prepared separately in 10 ml of heptane by consecutively introducing the Aluminum alkyl, MAO or TIOA/water (Al/H₂O=2.1), and after 5 minutes of stirring, the metallocene solved in toluene (the lowest amount as possible). After 5 minutes of stirring, the solution was introduced into the autoclave under ethylene flow. The reactor was closed, the temperature risen to 80° C. and pressurized with ethylene to 5.0 bar-g. The total pressure was kept constant by feeding ethylene. After the time indicated in Table 1, the polymerization was stopped by cooling, by degassing the reactor and by introducing 1 ml of ethanole. The achieved polymer was washed with acidic methanol, than with methanol and dried in an oven at 60° C. under vacuum.

The polymerization conditions and the characterization data of the polymer obtained are reported in Table 1.

Polymerization Example 4

The general procedure described in Examples 1–3 was followed, except that the polymerization was carried out in 100 ml hexane instead of heptane, the total pressure (Ptot) was 4.6 bar-g instead of 4.0 bar-g and the ethylene pressure PpC₂ 4.2 bar instead of 5.0 bar. The polymerization conditions and the data relating to the obtained polymer are indicated in Table 1.

Polymerization Example 5 (Comparison)

The general procedure described in Examples 1–3 was followed, except that the metallocene dimethylsilandiylbis(fluorenyl)zirconium dichloride was used.

The polymerization conditions and the data relating to the obtained polymer are indicated in Table 1.

Polymerization Examples 6 to 9
Ethylene/1-hexene copolymerization

In a 260 ml glass autoclave, provided with magnetic stirrer, temperature indicator and feeding line for ethylene was purified and fluxed with ethylene at 35° C. At room temperature it was introduced 1-hexene in the amount reported in table 2 and heptane to reach 140 ml of volume. The catalytic system was prepared separately in 10 ml of heptane by consecutively introducing the MAO (0.33 mmol) and the metallocene solved in 3 ml of toluene. After 5 minutes of stirring the solution was introduced into the autoclave under ethylene flow. The reactor was closed, the temperature risen to 70° C. and pressurized to 4.5 bar. The total pressure was kept constant by feeding ethylene. After 10 minutes the polymerization was stopped by cooling, by degassing the reactor and by introducing 1 ml of methanol. The achieved polymer was washed with acidic methanol, then with methanol and dried in an oven at 60° C. under vacuum.

The polymerization conditions and the data reacting to the obtained polymer are indicated in Tables 2 and 3.

Polymerization Example 10 (Comparison)

The general procedure described in Example 6–9 was followed, except that the polymerization was carried out with the metallocene dimethylsilandiylbis(fluorenyl)zirconium dichloride.

The polymerization conditions and the data relating to the obtained polymer are indicated in Tables 2 and 3.

Polymerization Examples 11 to 14
Ethylene/propylene-copolymerization

Polymerizations were performed at 50° C., in a 250 mL glass reactor, equipped with a mechanical stirrer, a thermometer and a pipe for monomers feeding. 100 mL of toluene and the TIOAO solution, fresh prepared as described above (3.45 mmol of Aluminum) was introduced in the nitrogen-purged reactor, kept in a thermostatic bath. At the polymerization temperature, an ethylene/propylene gaseous mixture (60% wt of ethylene) was fed and continuously discharged with a flow of 1.5 L/min and a pressure of 1.1 atm. After 2 minute, 3.45 μmol of catalyst, dissolved in 5 mL of toluene in the presence of 34 μmoles of TIOA, were added to start the polymerization. During the polymerization, the temperature was kept within ±0.2° C. The polymerization was stopped after 15 min by adding 1 mL of methanol and the copolymer was recovered by precipitation in methanol/HCl, filtered off, washed with methanol and finally dried at 50° C. under reduced pressure.

The polymerization conditions and the data relating to the obtained polymer are indicated in Table 4 and Table 5.

Polymerization Examples 15 to 18

Ethylene/propylene/ENB terpolymerization

Polymerizations were performed at 50° C., in a 250 mL glass reactor, equipped with a mechanical stirrer, a thermometer and a pipe for monomers feeding. 100 mL of toluene, 2 mL of ENB and 1.2 mL of MAO solution (2.0 mmol of Aluminum) were introduced in the nitrogen-purged reactor, kept in a thermostatic bath. At the polymerization temperature, a ethene/propylene gaseous mixture (60 wt % of ethene) was fed with a flow of 1.5 L/min and a pressure of 1.1 bar. After 2 minutes 2.0 µmol of catalyst, dissolved in 5 mL of toluene in the presence of 20 µmoles of MAO, were added to start the polymerization. During the polymerization, the temperature was kept within ±0.2° C. The polymerization was stopped after 15 min by adding 1 mL of methanol and the copolymer was recovered by precipitation in methanol/HCl, filtered off, washed with methanol and finally dried at 50° C. under reduced pressure.

The polymerization conditions and the data relating to the obtained polymer are indicated in Table 6 and Table 7.

Polymerization Examples 19 and 20

Ethylene/1-octene Gas Phase Polymerization 100 g of a polypropylene having I.V.=1.49 (dL/g), a poured density of 0.363 (g/cc) and a porosity by mercury of 0.375 cc/g, were charged into a 4.2 L reactor through a hole in the ceiling of the reactor, under propane atmosphere (pressure=1 bar), at room temperature, without any stirring. 250 g of propane were added and than temperature was brought to 40° C. In the meantime the 20 mg of metallocene, TIOA, and MAO (Al/Zr=200 mol/mol; MAO/TIOA: 1:5) were dissolved in an amount of toluene such that a total volume of 10 ml was reached, and stirred at room temperature for 10 minutes. The catalyst solution was then injected into the reactor by a little nitrogen overpressure. The suspension in the reactor was stirred at 40° C. for 10 minutes. The liquids present in the reactor were then flashed. 25 g of ethylene and 4.20 g of 1-octene were charged in the reactor, while temperature was brought to 75° C. The final pressure was 6 bar-g. During the polymerization reaction, the pressure was maintained constant by continuously feeding ethylene. During the polymerization reaction a 50 vol. % solution of 1-octene in pentane was continuously added dropwise. After the period of time indicated in table 8 the polymerization was stopped by quickly degassing the monomers. The polymer was collected and plunged in 800 mL of methanol, then filtered off and dried in vacuum at 60° C. for 2 hours.

The polymerization conditions and the data relating to the obtained polymer are indicated in Table 8.

Polymerization Example 21 Preparation of i-PP/EPM Reactor Blend with $Me_2Si(Me_4Cp)(7\text{-}MeTh_2\text{-}Cp)$. Gas Phase Process (i-PP carrier, 50° C. Propane)

In a 4.25-L stainless-steel stirred reactor at 30° C. in a propane atmosphere were charged 99.6 g of i-PP carrier (properties described in Table A below), 300 g of propane, then, by means of nitrogen overpressure, 1 mL of a 1 molar hexane solution of $Al(iso\text{-}octyl)_3$, and, after 5 minutes, the catalyst/cocatalyst mixture. The catalyst/cocatalyst mixture is prepared by dissolving the catalyst with MAO (Witco, toluene solution, 100 g/L, used as received), then adding a TIBA solution in hexane. The amounts used in the polymerization experiment are: 8 mg catalyst, 0.86 mL of the 100 g/L toluene solution of MAO (1.47 mmol Al), and 2.94 mL of a 1 molar solution of $Al(iso\text{-}octyl)_3$ in hexane (2.94 mmol Al). The solution is then diluted to 12 mL with hexane and aged 10 minutes at room temperature prior to injection into the reactor.

The reactor content is stirred at 40° C. for 10 min, then propane is vented in 5 min leaving a residual pressure of 4.5 bar-g at 30° C. The reactor is heated up to 50° C. in 5 min, while feeding 46 g of ethylene and 46 g of propylene to reach a pressure of 20 bar-g. Then the reactor is kept at 50° C. and a 60:40 wt % ethylene/propylene mixture is continuously fed for 26 min to maintain a constant pressure.

The monomers are vented, and the polymer collected and dried in a vacuum oven at 70° C. for 2 hours. 266 g of a spherical, free-flowing polymer is obtained, corresponding to 166.4 g of EPM rubber (63 wt %), whose properties are reported in Table B below.

TABLE A

| i-PP Carrier | |
|---|---|
| XSRT (% wt) | 2.2 |
| $T_m$ (° C.) | 162 |
| ΔH (J/g) | 100 |
| I.V. (dL/g) | 1.7 |
| Poured Density (g/mL) | 0.303 |

TABLE B

| | | |
|---|---|---|
| kg/g$_{cat}$ (min) | 21 (26) | |
| split (wt % EPM) | 63 | |
| Fouling (wt %) | 1 | |
| | whole | EPM |
| $C_2$ (wt %, IR) | 43.9 | 70.1 |
| I.V. (dL/g) | 1.86 | 1.96 |

TABLE 1

(ethylene homopolymerization)

| Example | Zirconocene dichloride type | (mg) | AlR$_3$ type | (mmol) | Al/Zr (mol) | Heptane (ml) | Time (min) | yield (g) | activity (Kg/gZr.h) | I.V. (dL/g) |
|---|---|---|---|---|---|---|---|---|---|---|
| 1 | Me$_2$Si(Me$_4$Cp)(7-MeTh$_2$—Cp) | 0.11 | MAO | 0.2 | 1055 | 150 | 15 | 4.48 | 973.1 | 7.5 |
| 2 | Me$_2$Si(2,7-tBu$_2$Cp)(7-MeTh$_2$—Cp) | 0.14 | MAO | 0.2 | 1122 | 150 | 15 | 2.55 | 560.0 | >12 |
| 3 | Me$_2$Si(7-MeTh$_2$—Cp)$_2$ | 0.13 | MAO | 0.2 | 1079 | 150 | 15 | 1.61 | 341.6 | >12 |
| 4** | Me$_2$Si(Flu)(7-MeTh$_2$—Cp) | 0.13 | MAO | 0.2 | 1020 | **) | 3 | 0.47 | 471.6 | 11.8 |
| 5 (comp) | Me$_2$Si(Flu)$_2$ | 0.48 | MAO | 0.4 | 1020 | 150 | 70 | 0.26 | 2.8 | 6.7 |

Polymerization conditions: 1-heptane, 150 ml, Al/H$_2$O = 2.1–2.2, 80° C., Ptot. 4.0 bar-g, PpC$_2$ 5.0 bar
**Polymerization conditions: 1-hexane, 100 ml, Al/H$_2$O = 2.1–2.2, 80° C., Ptot. 4.6 bar-g, PpC$_2$ 4.2 bar

TABLE 2

(ethylene/1-hexene copolymerization)

| Example | Zirconocene dichloride type | (mg) | AlR₃ type | Al/Zr (mmol) | 1-hexene (mol) | Time (ml) | yield (min) | activity (g) | I.V. (Kg/gZr.h) | (dL/g) |
|---|---|---|---|---|---|---|---|---|---|---|
| 6 | Me₂Si(7-MeTh₂—Cp)₂ | 0.13 | MAO | 0.22 | 1050 | 5 | 15 | 3.4 | 725.3 | 3.5 |
| 7 | Me₂Si(Flu)(7-MeTh₂—Cp) | 0.12 | MAO | 0.22 | 1090 | 2 | 15 | 1.9 | 419.4 | 5.3 |
| 8 | Me₂Si(2,7-tBu₂Cp)(7-MeTh₂—Cp) | 0.14 | MAO | 0.21 | 1050 | 2 | 15 | 3.1 | 689.2 | 4.5 |
| 9 | Me₂Si(Me₄Cp)(7-MeTh₂—Cp) | 0.11 | MAO | 0.2 | 1050 | 5 | 15 | 3.2 | 694.7 | 4.1 |
| 10 (comp) | Me₂Si(Flu)₂ | 0.3 | MAO | 0.60 | 1100 | 2 | 30 | 0.2 | 9.6 | 4.3 |

Polymerization conditions: heptane = 150 ml; cocatalyst = MAO; Temperature: 70° C.

TABLE 3

(ethylene/1-hexene copolymerization)

| | | | | N.M.R. | | | | |
|---|---|---|---|---|---|---|---|---|
| Example | Zirconocene dichloride | 1-hexene (mol %) | EHE | HHH (% mols) | HHE | EHE/ (EHE + HHE + HHH) | $r_1$ | $r_1 \cdot r_2$ |
| 6 | Me₂Si(7-MeTh₂—Cp)₂ | 11.8 | 11.5 | 0 | 0.32 | 0.97 | 4.52 | 0.09 |
| 7 | Me₂Si(Flu)(7-MeTh₂—Cp) | 5.51 | 5.51 | 0 | 0 | 1 | 4.21 | 0 |
| 8 | Me₂Si(2,7-tBu₂Cp)(7-MeTh₂—Cp) | 7.34 | 7.34 | 0 | 0 | 1 | 3.19 | 0 |
| 9 | Me₂Si(Me₄Cp)(7-MeTh₂—Cp) | 5.34 | 5.34 | 0 | 0 | 1 | 11.1 | 0 |
| 10 (comp) | Me₂Si(Flu)₂ | n.d | n.d | n.d | n.d | n.d | n.d | n.d | n.d. not determined
Tm (° C.): Ex. 6: 55; Ex. 7: 91; Ex. 8: 82; Ex. 9: 98; Ex. 10: 106;
ΔH (J/g): Ex. 6: 31; Ex. 7: 71; Ex. 8: 44; Ex. 9: 73; Ex. 10: 56;

TABLE 4

(ethylene/propylene copolymerization)

| Example | Zirconocene dichloride | Zr (μmoles) | yield (g) | activity (Kg/gZr · h) | I.V. (dL/g) |
|---|---|---|---|---|---|
| 11 | Me₂Si(7-MeTh₂—Cp)₂ | 3.45 | 0.3 | 3.81 | 1.0 |
| 12 | Me₂Si(Flu)(7-MeTh₂—Cp) | 3.45 | 1.3 | 16.5 | 1.8 |
| 13 | Me₂Si(2,7-tBu₂Cp)(7-MeTh₂—Cp) | 3.45 | 3 | 38.1 | 2.0 |
| 14 | Me₂Si(Me₄Cp)(7-MeTh₂—Cp) | 1.17 | 0.8 | 30.0 | 3.8 |

TABLE 5

(ethylene/propylene copolymerization)

| | | | | N.M.R. | | | |
|---|---|---|---|---|---|---|---|
| Example | Zirconocene dichloride | C₂ (mol %) | EPE | PPP (% mols) | PPE | EPE/ (EPE + PPE + PPP) | $r_1 \cdot r_2$ |
| 11 | Me₂Si(7-MeTh₂—Cp)₂ | 74.0 | 23.04 | 0 | 2.92 | 0.89 | 0.12 |
| 12 | Me₂Si(Flu)(7-MeTh₂—Cp) | 73.7 | 24.61 | 0 | 1.73 | 0.93 | 0.07 |
| 13 | Me₂Si(2,7-tBu₂Cp)(7-MeTh₂—Cp) | 68.6 | 28.69 | 0 | 2.46 | 0.92 | 0.05 |
| 14 | Me₂Si(Me₄Cp)(7-MeTh₂—Cp) | 91.4 | 8.64 | 0 | 0 | 1 | 0 |

TABLE 6

(ethylene/propylene/ENB polymerization)

| Example | Zirconocene dichloride | Zr (μmoles) | yield (g) | activity (Kg/gZr · h) | I.V. (dL/g) |
|---|---|---|---|---|---|
| 15 | Me₂Si(7-MeTh₂—Cp)₂ | 2.6 | 0.1 | 1.7 | 0.6 |
| 16 | Me₂Si(Flu)(7-MeTh₂—Cp) | 2.6 | 0.2 | 3.4 | 0.6 |
| 17 | Me₂Si(2,7-tBu₂Cp)(7-MeTh₂—Cp) | 2.6 | 0.2 | 3.4 | 1.0 |
| 18 | Me₂Si(Me₄Cp)(7-MeTh₂—Cp) | 2.6 | 2.1 | 35.4 | 1.85 |

TABLE 7

(ethylene/propylene/ENB polymerization)

| | | | | N.M.R. | | | |
|---|---|---|---|---|---|---|---|
| Example | Zirconocene dichloride | ENB (mol %) | E (mol %) | EPE | PPP (% mols) | PPE | EPE/ (EPE + PPE + PPP) |
| 15 | Me$_2$Si(7-MeTh$_2$—Cp)$_2$ | 2.47 | 74.00 | n.d. | n.d. | n.d. | n.d. |
| 16 | Me$_2$Si(Flu)(7-MeTh$_2$—Cp) | 1.01 | 76.54 | n.d. | n.d. | n.d. | n.d. |
| 17 | Me$_2$Si(2,7-tBu$_2$Cp)(7-MeTh$_2$—Cp) | 0.38 | 72.73 | n.d. | n.d. | n.d. | n.d. |
| 18 | Me$_2$Si(Me$_4$Cp)(7-MeTh$_2$—Cp) | 0.54 | 85.50 | 10.5 | 0 | 0 | 1 | n.d. not determined

TABLE 8

(ethylene/1-octene gas phase polymerization)

| | Zirconocene dichloride | | C2 feed | C8 feed | Time | Yield | activity | C$_8$ units | I.V. |
|---|---|---|---|---|---|---|---|---|---|
| Example | Type | (mg) | (g) | (g) | (min) | (g) | (Kg/gcat) | (wt %) | (dL/g) |
| 19 | Me$_2$Si(Flu)(7-MeTh$_2$—Cp) | 20 | 80 | 12 | 180 | 90 | 4.5 | 14 | 2.46 |
| 20 | Me$_2$Si(2,7-tBu$_2$Cp)(7-MeTh$_2$—Cp) | 20 | 130 | 21 | 30 | 156 | 7.8 | 12 | 3.93 |

What is claimed is:

1. A process for the preparation of a ligand of formula (V):

$$SiR^1R^2Q'L' \quad (V)$$

wherein

R$^1$ and R$^2$, the same or different from each other, are selected from hydrogen, a C$_1$–C$_{20}$-alkyl, C$_3$–C$_{20}$-cycloalkyl, C$_2$–C$_{20}$-alkenyl, C$_6$–C$_{20}$-aryl, C$_7$–C$_{20}$-alkylaryl or C$_7$–C$_{20}$-arylalkyl radical, optionally containing heteroatoms belonging to groups 13 or 15–17 of the Periodic Table of the Elements; optionally R$^1$ and R$^2$ form a ring comprising from 3 to 8 atoms, which can bear substituents;

Q' is a moiety of the general formula (VI):

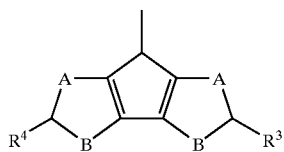

(VI)

or its double bond isomers, wherein A and B are selected from sulfur (S), oxygen (O) or CR$^5$, R$^5$ being selected from hydrogen, a C$_1$–C$_{20}$-alkyl, C$_3$–C$_{20}$-cycloalkyl, C$_2$–C$_{20}$-alkenyl, C$_6$–C$_{20}$aryl, C$_7$–C$_{20}$-alkylaryl or C$_7$–C$_{20}$-arylalkyl radicals optionally containing heteroatoms belonging to groups 13 or 15–17 of the Periodic Table of the Elements; either A or B being different from CR$^5$, and wherein the rings containing A and B have a double bond in the allowed position having an aromatic character; if A is S or O, B is CR$^5$ or if B is S or O, A is CR$^5$;

R$^3$ and R$^4$, the same or different from each other, are selected from hydrogen, a C$_1$–C$_{20}$-alkyl, C$_3$–C$_{20}$-cycloalkyl, C$_2$–C$_{20}$-alkenyl, C$_6$–C$_{20}$-aryl, C$_7$–C$_{20}$-alkylaryl or C$_7$–C$_{20}$-arylalkyl optionally containing heteroatoms belonging to groups 13 or 15–17 of the Periodic Table of the Elements;

L' is a moiety of the general formula (VII):

(VII)

or its double bond isomers, wherein R$^6$, R$^7$, R$^8$ and R$^9$, the same or different from each other, are selected from C$_1$–C$_{20}$-alkyl, C$_3$–C$_{20}$-cycloalkyl, C$_2$–C$_{20}$-alkenyl, C$_6$–C$_{20}$-aryl, C$_7$–C$_{20}$-alkylaryl or C$_7$–C$_{20}$-arylalkyl radicals optionally containing heteroatoms belonging to groups 13 or 15–17 of the Periodic Table of the Elements; and at least two adjacent R$^6$ and R$^7$ or R$^8$ and R$^9$ can form a ring comprising from 3 to 8 atoms, optionally bearing substituents and optionally containing heteroatoms belonging to groups 13 or 15–17 of the Periodic Table of the Elements;

comprising the following steps:

i) treating a compound of formula (VIII) with at least one equivalent of a base selected from the group consisting of metallic sodium and potassium, sodium and potassium hydroxide and an organolithium compound;

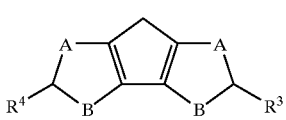

(VIII)

wherein the rings containing A and B have a double bond in the allowed position having an aromatic character; A, B, R$^3$ and R$^4$ are defined as above;

ii) contacting the corresponding anionic compound obtained from step i) with a compound of general formula (IX):

 (IX)

wherein L', R$^1$, R$^2$ have the meaning described above and Y is a halogen atom selected from the group consisting of fluoride, chloride, bromide and iodide.

2. A process for the preparation of a ligand of formula (V):

 (V)

wherein

R$^1$ and R$^2$, the same or different from each other, are selected from hydrogen, a C$_1$–C$_{20}$-alkyl, C$_3$–C$_{20}$-cycloalkyl, C$_2$–C$_{20}$-alkenyl, C$_6$–C$_{20}$-aryl, C$_7$–C$_{20}$-alkylaryl or C$_7$–C$_{20}$-arylalkyl radical, optionally containing heteroatoms belonging to groups 13 or 15–17 of the Periodic Table of the Elements; optionally R$^1$ and R$^2$ form a comprising from 3 to 8 atoms, which can bear substituents;

Q' is a moiety of the general formula (VI):

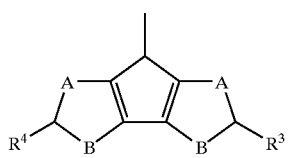 (VI)

or its double bond isomers, wherein A and B are selected from sulfur (S), oxygen (O) or CR$^5$, R$^5$ being selected from hydrogen, a C$_1$–C$_{20}$-alkyl, C$_3$–C$_{20}$-cycloalkyl, C$_2$–C$_{20}$-alkenyl, C$_6$–C$_{20}$-aryl, C$_7$–C$_{20}$-alkylaryl or C$_7$–C$_{20}$-arylalkyl radicals optionally containing heteroatoms belonging to groups 13 or 15–17 of the Periodic Table of the Elements; either A or B being different from CR$^5$, and wherein the rings containing A and B have a double bond in the allowed position having an aromatic character; if A is S or O, B is CR$^5$ or if B is S or O, A is CR$^5$;

R$^3$ and R$^4$, the same or different from each other, are selected from hydrogen, a C$_1$–C$_{20}$-alkyl, C$_3$–C$_{20}$-cycloalkyl, C$_2$–C$_{20}$-alkenyl, C$_6$–C$_{20}$-aryl, C$_7$–C$_{20}$-alkylary or C$_7$–C$_{20}$-arylalkyl optionally containing heteroatoms belonging to groups 13 or 15–17 of the Periodic Table of the Elements;

L' is a moiety of the general formula (VII):

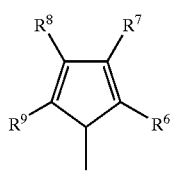 (VII)

or its double bond isomers, wherein R$^6$, R$^7$, R$^8$ and R$^9$, the same or different from each other, are selected from C$_1$–C$_{20}$-alkyl, C$_3$–C$_{20}$-cycloalkyl, C$_2$–C$_{20}$-alkenyl, C$_6$–C$_{20}$-aryl, C$_7$–C$_{20}$-alkylaryl or C$_7$–C$_{20}$-arylalkyl radicals optionally containing heteroatoms belonging to groups 13 or 15–17 of the Periodic Table of the Elements; and at least two adjacent R$^6$ and R$^7$ or R$^8$ and R$^9$ can form a ring comprising from 3 to 8 atoms, optionally bearing substituents and optionally containing heteroatoms belonging to groups 13 or 15–17 of the Periodic Table of the Elements;

comprising the following steps:

i) treating a compound of formula (VIII) with at least one equivalent of a base selected from the group consisting of metallic sodium and potassium, sodium and potassium hydroxide and an organolithium compound;

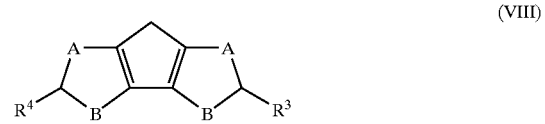 (VIII)

wherein the rings containing A and B have a double bond in the allowed position having an aromatic character, A, B, R$^3$ and R$^4$ are defined as above;

ii) contacting the corresponding anionic compound obtained from step i) with a compound of general formula (X):

 (X)

wherein L', R$^1$, R$^2$ have the meaning described above and Y is a halogen atom selected from the group consisting of fluoride, chloride, bromide and iodide;

iii) contacting the product obtained in step ii) with a compound of formula (XI):

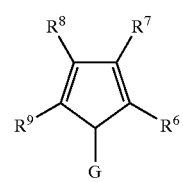 (XI)

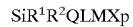

wherein R$^6$, R$^7$, R$^8$ and R$^9$ have the meaning reported above and G is sodium, potassium or lithium.

3. A process for the preparation of a metallocene of the general formula (I):

SiR$^1$R$^2$QLMX$_p$ (I)

wherein SiR$^1$R$^2$ is a divalent group bridging the moieties L and Q;

R$^1$ and R$^2$, the same or different from each other, are selected from hydrogen, a C$_1$–C$_{20}$-alkyl, C$_3$–C$_{20}$-cycloalkyl, C$_2$–C$_{20}$-alkenyl, C$_6$–C$_{20}$-aryl, C$_7$–C$_{20}$-alkylaryl or C$_7$–C$_{20}$-arylalkyl radical optionally containing heteroatoms belonging to groups 13 or 15–17 of the Periodic Table of the Elements; optionally R$^1$ and R$^2$ form a ring comprising from 3 to 8 atoms, which can bear substituents;

Q is a moiety of formula (II):

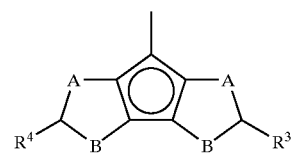 (II)

wherein A and B are selected from sulfur (S), oxygen (O) or CR$^5$, R$^5$ being selected from hydrogen, a C$_1$–C$_{20}$- alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals optionally containing heteroatoms belonging to groups 13 or 15–17 of the Periodic Table of the Elements; either A or B being different from $CR^5$, and wherein the rings containing A and B have a double bond in the allowed position having an aromatic character; if A is S or O, B is $CR^5$ or if B is S or O, A is $CR^5$;

$R^3$ and $R^4$, the same or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl optionally containing heteroatoms belonging to groups 13 or 15–17 of the Periodic Table of the Elements;

L is a moiety of formula (III):

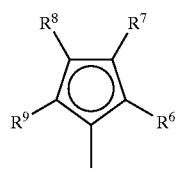

(III)

wherein $R^6$, $R^7$, $R^8$ and $R^9$, the same or different from each other, are selected from $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals optionally containing heteroatoms belonging to groups 13 or 15–17 of the Periodic Table of the Elements; and at least two adjacent $R^6$ and $R^7$ or $R^8$ and $R^9$ can form a ring comprising from 3 to 8 atoms, optionally bearing substituents and optionally containing heteroatoms belonging to groups 13 or 15–17 of the Periodic Table of the Elements;

M is an atom of a transition metal selected from those belonging to group 3, 4, 5, 6 or to the lanthanide or actinide groups in the Periodic Table of the Elements, X, the same or different from each other, is a ligand selected from hydrogen, halogen, $R^{10}$, $OR^{10}$, $OSO_2CF_3$, $OCOR^{10}$, $SR^{10}$, $NR^{10}_2$ or $PR^{10}_2$ group, wherein $R^{10}$ is selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radical, optionally containing heteroatoms belonging to groups 13 or 15–17 of the Periodic Table of the Elements; p is an integer of from 1 to 3, being equal to the oxidation state of the metal M minus 2;

comprising the following steps:
a) contacting a ligand of formula (V):

$SiR^1R^2Q'L'$ (V)

wherein
Q' is a moiety of the general formula (VI):

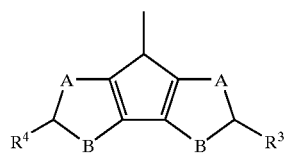

(VI)

or its double bond isomers, wherein A, B, $R^3$ and $R^4$ are defined as above;

and L' is a moiety of the general formula (VII):

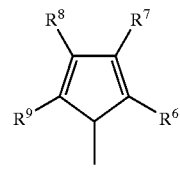

(VII)

or its double bond isomers, wherein $R^6$, $R^7$, $R^8$ and $R^9$ are defined as above; with a base, wherein the ratio between said base and the compound of formula (V) is at least 2, b) contacting the obtained product with a compound of formula $MX_{p+2}$, wherein M, X and p are defined as above.

4. A metallocene compound of formula (I)

$SiR^1R^2LQMXp$ (I)

wherein $SiR^1R^2$ is a divalent group bridging the moieties L and Q;

$R^1$ and $R^2$, the same or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radical optionally containing heteroatoms belonging to groups 13 or 15–17 of the Periodic Table of the Elements; optionally $R^1$ and $R^2$ form a ring comprising from 3 to 8 atoms, which can bear substituents;

Q is a moiety of formula (II):

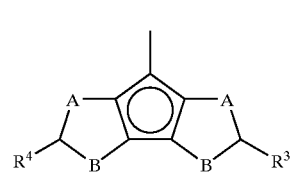

(II)

wherein A and B are selected from sulfur (S), oxygen (O) or $CR^5$, $R^5$ being selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals optionally containing heteroatoms belonging to groups 13 or 15–17 of the Periodic Table of the Elements; either A or B being different from $CR^5$, and wherein the rings containing A and B have a double bond in the allowed position having an aromatic character; if A is S or O, B is $CR^5$ or if B is S or O, A is $CR^5$;

$R^3$ and $R^4$, the same or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl optionally containing heteroatoms belonging to groups 13 or 15–17 of the Periodic Table of the Elements;

L is a moiety of formula (III):

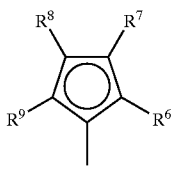

(III)

wherein $R^6$, $R^7$, $R^8$ and $R^9$, the same or different from each other, are selected from $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals optionally containing heteroatoms belonging to groups 13 or 15–17 of the Periodic Table of the Elements; and at least two adjacent $R^6$ and $R^7$ or $R^8$ and $R^9$ can form a ring comprising from 3 to 8 atoms, optionally bearing substituents and optionally containing heteroatoms belonging to groups 13 or 15–17 of the Periodic Table of the Elements;

M is an atom of a transition metal selected from those belonging to group 3, 4, 5, 6 or to the lanthanide or actinide groups in the Periodic Table of the Elements, X, the same or different from each other, is a ligand selected from hydrogen, halogen, $R^{10}$, $OR^{10}$, $OSO_2CF_3$, $OCOR^{10}$, $SR^{10}$, $NR^{10}{}_2$, or $PR^{10}{}_2$ group, wherein $R^{10}$ is selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radical, optionally containing heteroatoms belonging to groups 13 or 15–17 of the Periodic Table of the Elements; p is an integer of from 1 to 3, being equal to the oxidation state of the metal M minus 2.

5. A ligand of formula (V):

$SiR^1R^2Q'L'$ (V)

wherein $R^1$ and $R^2$, the same or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radical, optionally containing heteroatoms belonging to groups 13 or 15–17 of the Periodic Table of the Elements; optionally $R^1$ and $R^2$ form a ring comprising from 3 to 8 atoms, which can bear substituents;

Q' is a moiety of the general formula (VI):

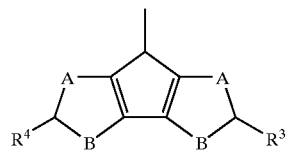

(VI)

or its double bond isomers, wherein A and B are selected from sulfur (S), oxygen (O) or $CR^5$, $R^5$ being selected from hydrogen, a $C_1$–$C_{20}$alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals optionally containing heteroatoms belonging to groups 13 or 15–17 of the Periodic Table of the Elements; either A or B being different from $CR^5$, and wherein the rings containing A and B have a double bond in the allowed position having an aromatic character; if A is S or O, B is $CR^5$ or if B is S or O, A is $CR^5$;

$R^3$ and $R^4$, the same or different from each other, are selected from hydrogen, a $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl optionally containing heteroatoms belonging to groups 13 or 15–17 of the Periodic Table of the Elements;

L' is a moiety of the general formula (VII);

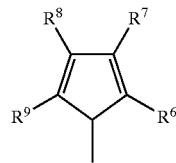

(VII)

or its double bond isomers, wherein $R^6$, $R^7$, $R^8$ and $R^9$, the same or different from each other, are selected from $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals optionally containing heteroatoms belonging to groups 13 or 15–17 of the Periodic Table of the Elements; and at least two adjacent $R^6$ and $R^7$ or $R^8$ and $R^9$ can form a ring comprising from 3 to 8 atoms, optionally bearing substituents and optionally containing heteroatoms belonging to groups 13 or 15–17 of the Periodic Table of the Elements.

* * * * *

UNITED STATES PATENT AND TRADEMARK OFFICE
CERTIFICATE OF CORRECTION

PATENT NO.    : 6,822,106 B2
DATED         : November 23, 2004
INVENTOR(S)   : Tiziano Dall'Occo et al.

It is certified that error appears in the above-identified patent and that said Letters Patent is hereby corrected as shown below:

Column 29,
Line 20, after "form a" insert -- ring --.

Signed and Sealed this

Twenty-seventh Day of September, 2005

JON W. DUDAS
*Director of the United States Patent and Trademark Office*